(12) United States Patent
Martinetti et al.

(10) Patent No.: US 8,172,907 B2
(45) Date of Patent: May 8, 2012

(54) METHOD FOR THE PRODUCTION OF A BIOLOGICALLY ACTIVE PROSTHETIC DEVICE FOR THE RECONSTRUCTION OF BONE TISSUE AND THE PROSTHETIC DEVICE ITSELF

(75) Inventors: Roberta Martinetti, Forli (IT); Angelo Nataloni, Castel Bolognese (IT); Andrea Belpassi, Urbino (IT)

(73) Assignee: Fin-Ceramica Faenza S.p.A., Faenza (IT)

( * ) Notice: Subject to any disclaimer, the term of this patent is extended or adjusted under 35 U.S.C. 154(b) by 818 days.

(21) Appl. No.: 10/594,941

(22) PCT Filed: Mar. 29, 2005

(86) PCT No.: PCT/IB2005/000852
§ 371 (c)(1),
(2), (4) Date: Mar. 13, 2008

(87) PCT Pub. No.: WO2005/094730
PCT Pub. Date: Oct. 13, 2005

(65) Prior Publication Data
US 2008/0243458 A1  Oct. 2, 2008

(30) Foreign Application Priority Data
Mar. 30, 2004 (EP) .................................... 04425224

(51) Int. Cl.
*A61F 2/28* (2006.01)
*B29C 33/40* (2006.01)

(52) U.S. Cl. ...................... 623/23.56; 264/219; 264/227; 700/98; 700/119

(58) Field of Classification Search .................. 600/407; 264/222, 219, 227; 345/419, 420; 700/119, 700/98
See application file for complete search history.

(56) References Cited

U.S. PATENT DOCUMENTS

| | | | |
|---|---|---|---|
| 5,490,962 A * | 2/1996 | Cima et al. | 264/401 |
| 5,741,215 A | 4/1998 | D'Urso | |
| 6,112,109 A | 8/2000 | D'Urso | |
| 2002/0169066 A1 | 11/2002 | Cassidy et al. | |
| 2003/0006534 A1 * | 1/2003 | Taboas et al. | 264/401 |
| 2004/0152034 A1 * | 8/2004 | Cummings et al. | 433/8 |

FOREIGN PATENT DOCUMENTS

| | | |
|---|---|---|
| EP | 1 411 035 A2 | 4/2004 |
| IT | 1 307 292 | 10/2001 |
| WO | WO 02/083188 | 8/2003 |

* cited by examiner

*Primary Examiner* — Thomas J Sweet
*Assistant Examiner* — Jason-Dennis Stewart
(74) *Attorney, Agent, or Firm* — Pearne & Gordon LLP

(57) ABSTRACT

The invention relates to a method for the production of a biologically active prosthetic device for the reconstruction of bone tissue comprising the steps of: a CAT (Computerized Axial Tomography) scan of the patient and obtaining a three-dimensional electronic model (1) of the part of the bone and of a bone defect (2) to be reconstructed; production by prototyping of a prototype resin model (3) of the area of the patient's bone involved, forming of a model (4), of the patient's bone defect to be reconstructed; construction of a netative mould (5), production of a ready sintered ceramic semi-finished product with controlled and interconnected porosity, said semi-finished product being made with dimensions and shape slightly larger than the bone defect; mechanical processing and manual finishing of the sintered semi-finished product, to obtain the precise dimensions and shape of the bone defect, the invention also relating to the prosthetic device obtained using the method described above.

10 Claims, 2 Drawing Sheets

FIG. 1
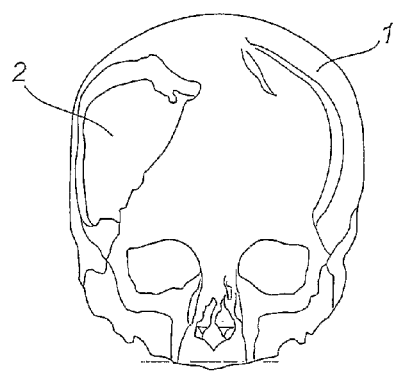
FIG. 2
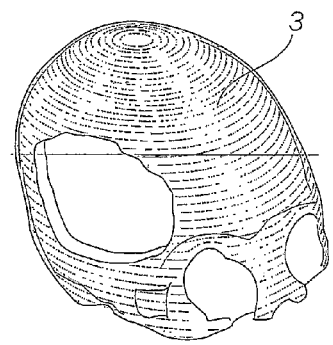
FIG. 3
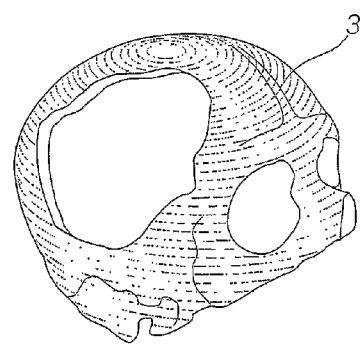
FIG. 4
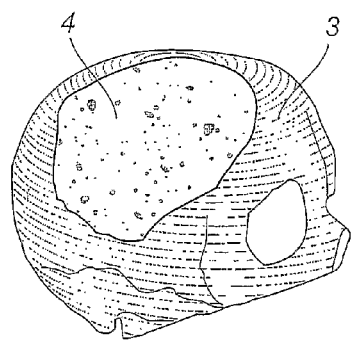
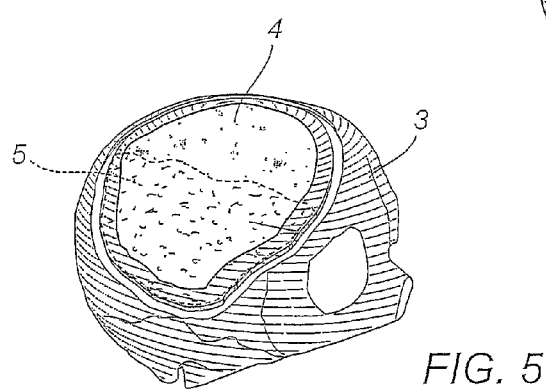
FIG. 5

METHOD FOR THE PRODUCTION OF A BIOLOGICALLY ACTIVE PROSTHETIC DEVICE FOR THE RECONSTRUCTION OF BONE TISSUE AND THE PROSTHETIC DEVICE ITSELF

The present invention relates to a method for the production of a biologically active prosthetic device for the reconstruction of bone tissue and the prosthetic device itself.

More specifically, the method according to the present invention involves obtaining a made to measure prosthetic device identical to a bone defect or lacuna to be filled in a patient, and which is made of a biologically active material, that is to say, a Ca/P-based ceramic synthesis material (calcium phosphate material, i.e.: stoichiometric hydroxyapatite; non-stoichiometric hydroxyapatite: carbonated hydroxyapatite (mainly of type B); hydroxyapatite enriched with magnesium or fluoride or with strontium or sodium; carbonated hydroxyapatite enriched with magnesium; hydroxyapatite/$\beta$ tricalcium phosphate in proportions of 50%-50%, 70%-30%, 30%-70%; alpha-tricalcium phosphate ($\alpha$TCP); beta-tricalcium phosphate ($\beta$TCP); mixtures of alpha-tricalcium phosphate ($\alpha$TCP) and beta-tricalcium phosphate ($\beta$TCP) with predetermined and interconnected porosity in the 30-90% range with bimodal distribution of the dimensions of the pores in the 0.1-125 microns and 125-2500 microns range. The prosthetic device according to the present invention is obtained with a new production technology and is used for a new bone reconstruction technique.

Having achieved the primary objective of saving the patient's life, in its latest scientific and technological evolution, surgery aims in its most advanced area of development to improve the patient's quality of life, making the surgical solutions adopted more acceptable for the patient in functional and aesthetic terms.

It is currently possible to carry out operations substituting both hard tissue and very extensive tissue.

In parallel, biotechnologies, with great progress made in molecular biology, have undergone enormous growth particularly in the last decade.

Genetic engineering and prosthetic engineering were a driving force behind research and development of new systems for the production of medical devices, in terms of both materials and components, to allow clinical solutions whose size and quality are suitable for the individual, specific patient and are the main driving forces in the field of biomedical research for this type of clinical applications.

At present in the reconstruction of lacunae in bones, such as parts of the cranium, maxillofacial zones or parts of long bones (for example the femur), parts of bone are used which are taken from the patient (autologous transplant) or from other persons (heterologous transplant) or artificial materials such as: metals (gold, steel, titanium, tantalum) in the form of plates or meshes or in elongated form, polymers (Nylon, Polyethylene), cements (PMMA: polymethyl methacrylate) and porous bio-ceramic materials, for example ceratite and hydroxyapatite.

Each of these materials has pros and cons, but as a whole porous bio-ceramic materials have some important advantages: the possibility of practically unlimited supplies, unlike transplants using biological materials (autologous or heterologous bone) in which the bone to be used must be taken from the patient or a donor, the fact that they are biologically active materials and so promote bone regeneration, and the quality of being recognised as inorganic material not alien to the patient and so free of the problems of rejection.

There are basically two types of surgical reconstruction techniques: manual modelling during an operation of the prosthetic device which must be implanted and must fill the lacuna in the bone, or it is possible to implant a prosthetic device already produced and modelled to size for the specific lacuna in the patient's bone before the operation.

The fact that a prosthetic device to be substituted is already ready with the shape and dimensions made to measure for the patient's lacuna makes the surgery much faster and simpler, however, the production of a prosthetic device with shape and dimensions already suitable for the patient's specific lacuna involves difficulties, and the current technique for the production of these devices does not yet give satisfactory results when the above-mentioned bio-ceramic materials are used.

More precisely, due to the intrinsic characteristics and porosity of the above-mentioned bio-ceramic materials, when a substitute part for a lacuna in a bone is slip cast using bio-ceramic material, it is difficult to obtain a part with the allocated shape and dimensions.

In particular, it is difficult to obtain a part which precisely substitutes a lacuna in a bone to be filled because the above-mentioned bio-ceramic materials are subject to variations in shape and size retraction during both drying after slip casting and after firing.

One aim of the present invention is to present an improved method for the production of a prosthetic device for the reconstruction of bone tissue with size and shape characteristics identical to the section of bone missing from the patient without the need for adaptations during insertion of the prosthetic device.

Another aim of the present invention is to present an improved method for the production of a prosthetic device for the reconstruction of bone tissue which is made of biologically active material with a controlled-porosity ceramic component.

In accordance with one aspect of the present invention, a method is proposed for the production of a prosthetic device for the reconstruction of bone tissue as specified in claim 1.

Yet another aim of the present invention is the production of a prosthetic device made of biologically active material with a ceramic component having controlled and interconnected porosity in the 30-90% range, with bimodal distribution of the dimensions of the pores in the 0.1-125 microns and 125-2500 microns range, and with bioactivity characteristics, through which the osteoconductive properties of the Ca/P-based material, able to contribute to bone regeneration mechanisms, so as to promote the laying down and regrowth of bone tissue.

In accordance with another aspect of the present invention, a prosthetic device is proposed which is made of biologically active material with a porous structure as specified in claim 8.

The dependent claims refer to preferred and advantageous embodiments of the invention.

Embodiments of the present invention, shown by way of example only and without limiting the scope of the invention, are described below with reference to the accompanying drawings, in which:

FIG. 1 illustrates a computer model of a patient's cranium in which there is a lacuna in the bone;

FIGS. 2 and 3 illustrate a resin model obtained from the computer model shown in the previous figure;

FIGS. 4 and 5 illustrate two successive steps of the method in accordance with the present invention;

Figure 7:
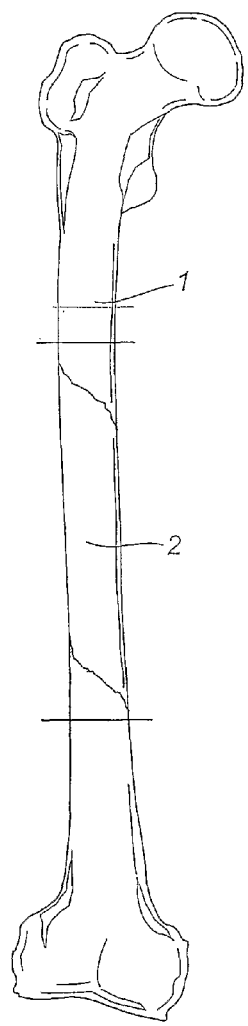
FIG. 7 illustrates another application of the present invention relative to long bones, for example a femur, in particular illustrating a patient's femur with a missing central part.
Figure 8:
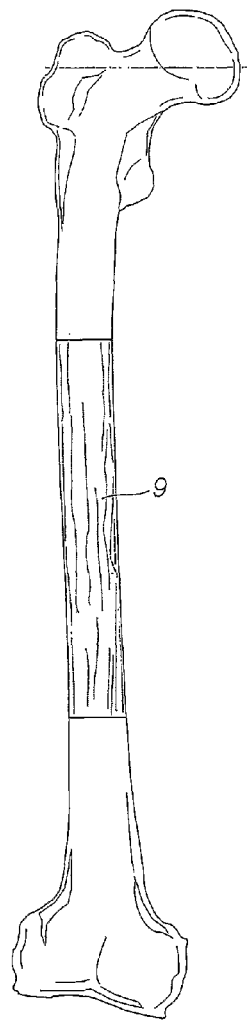
FIG. 8 illustrates the femur shown in the previous figure with a prosthetic device in accordance with the present invention.
Figure 9:
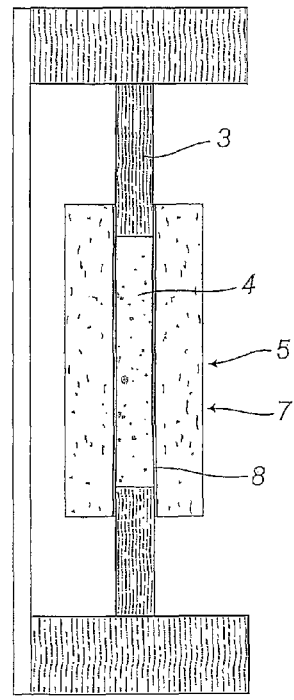
FIG. 9 is a front view of a computer model of the femur illustrated in the previous figures with the central part missing (a lacuna in the bone) and a control mould for a prosthetic device.
Figure 10:
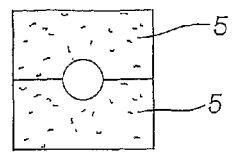
FIG. 10 is a cross-section of the mould illustrated in the previous figure.

The method for the production of a prosthetic device for the reconstruction of bone tissue in accordance with the invention basically comprises the following steps:

1. CAT (Computerised Axial Tomography) scan of the patient and creation of a CAT file representing the three-dimensional electronic model 1 (FIGS. 1 and 7) of the part of the bone and the bone defect 2 to be reconstructed;
2. based on the data obtained from the CAT (Computerised Axial Tomography) scan of the patient and the CAT file, rapid main and interface software system controlled prototyping is used to create a prototype resin model 3 (FIGS. 2, 3 and 9) of the area of the patient's bone involved, for example the model 3 may be obtained using the three-dimensional stereolithographic technique;
3. this resin prototype is used to make, with slip casting forming technology, the model 4 (in calcium sulphate, resins or silicone rubbers) of the patient's bone defect to be reconstructed;
4. the model in the previous point is used to make a mould 5 (FIGS. 5, 6, 9 and 10) out of calcium sulphate, resins or silicone rubbers which is a negative of the patient's bone defect, again using slip casting forming technology. To obtain this mould a kind of barrier 6 (FIGS. 5 and 6) or a containment mould 7 (FIG. 9) is made using suitable material (for example clay, plasticine or modelling paste) around the bone defect 2 area. The mould 5 made of calcium sulphate, resins or silicone rubbers is then slip cast in this barrier 6 (or containment mould 7) and will serve as a control for the shape and dimensions of the prosthetic device. For said control, the mould 5 has means 8 (FIGS. 6 and 9) able to detect any points of contact between the semi-finished product and the mould 5. These means 8 may be, for example a coating of tracing paper which can be coloured at points of contact;
5. production of a semi-finished product (not illustrated) already sintered, with controlled and interconnected porosity (30-90%) having pore dimensions in the 0.1-125 microns and 125-2500 microns range made of Ca/P-based biologically active ceramic materials. These materials may be the material described in Italian patent IT-1 307 292 or the material described in the application for a European patent EP-1 411 035 (and in the corresponding application for an Italian patent BO2002A000650). During this step the semi-finished product is made with dimensions larger than and shapes close to those of the model of the patient's bone defect;
6. mechanical processing and manual finishing of the sintered semi-finished product with controlled and interconnected porosity (30-90%) with bimodal distribution of the dimensions of the pores in the 0.1-125 microns and 125-2500 microns range, made of Ca/P-based ceramic material using as a shape and size comparator the negative mould of the patient's bone defect (point 4), to obtain a finished ceramic component corresponding to the patient's bone defect to be filled; mechanical processing and finishing are carried out by removing excess material with diamond milling cutters;
7. the final check of the finished ceramic component, that is to say, the prosthetic device 9 (FIG. 8), in terms of dimensions and shape, is carried out directly on the resin model of the area of the patient's bone involved—made in point 2—and using the negative mould 6 or 7 obtained in point 4.

It should be noticed that the mechanical processing for removal of material which allows obtainment of the dimensions and shape of the prosthetic device which must fill the bone defect is necessary because Ca/P-based porous ceramic material cannot be slip cast directly with the shape and dimensions required because it is subject to retraction and variations in shape which cannot be foreseen.

Therefore, a part must be made of porous ceramic material which is close to but slightly larger than the required shape and dimensions of the bone defect to be reconstructed.

The shape and precise dimensions of the prosthetic device 9 will then be achieved by means of successive approximations by manually removing material with diamond milling cutters which turn at high speed. Removal of material must be manual because porous ceramic material does not withstand mechanical processing by machine tools, for example, those of the numeric control type, since it would break.

Manual processing to remove material is essential because only an expert operator has the sensitivity required to avoid breaking the ceramic material. The check to ensure that the shape and precise dimensions of the prosthetic device 9 have been achieved takes place as indicated above with successive checks on the resin model 3 and with the aid of the control mould 5 and the means 8 able to detect any points of contact between the semi-finished product and the mould 5.

The prosthetic device disclosed is characterised in particular by the following aspects:

the shape and dimensions derive from a model of the area of the patient's bone involved, the model being obtained using rapid prototyping technology; its structure has a predetermined and interconnected porosity (30-90%) with bimodal distribution of the dimensions of the pores in the 0.1-125 microns and 125-2500 microns range, and is made of Ca/P-based ceramic synthesis material (Hydroxyapatite, Tricalcium Phosphate or mixtures of them) using technologies for the impregnation/imbibition of porous supports (cellulose, polyurethane, resin), gel-casting, low pressure injection moulding.

Figure 6:
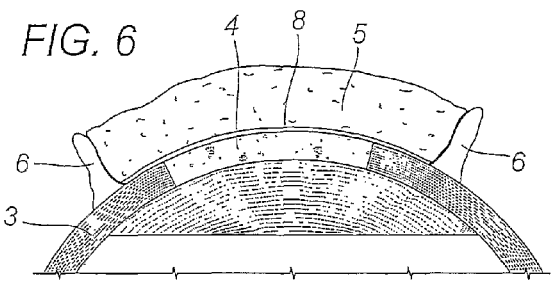
FIG. 6 is a cross-section of the cranium illustrated in the previous figures during the step relative to FIG. 5.

The production process flow refers to the following steps:

CAT scan of the patient and creation of the CAT file (FIG. 1);

reading of the CAT file and check of the extent of the bone defect;

production of the model of the area of the patient's bone involved using resin with rapid prototyping (FIGS. 2 and 3);

production of the model of the bone defect using calcium sulphate, resins or silicone rubbers (FIG. 4);

production of a negative mould of the bone defect using calcium sulphate, resins or silicone rubbers (FIGS. 5 and 6);

production of a sintered semi-finished product with dimensions greater than and shape similar to the bone defect, having controlled and interconnected porosity (30-90%) with pore dimensions in the 0.1-125 microns and 125-2500 microns range, using Ca/P-based ceramic material;

mechanical processing for removal of material and finishing of the porous ceramic component;

check of the size and shape of the porous ceramic component on the resin model of the area of the bone involved and with the negative of the bone defect;

washing, drying and packaging of the porous ceramic component;

sterilisation with gamma rays.

The materials which can be used to make the prosthetic device disclosed are:
stoichiometric hydroxyapatite; non-stoichiometric hydroxyapatite: carbonated hydroxyapatite (mainly of type B); hydroxyapatite enriched with magnesium or fluoride or with strontium or sodium; carbonated hydroxyapatite enriched with magnesium; hydroxyapatite/β tricalcium phosphate in proportions of 50%-50%, 70%-30%, 30%-70%; alpha-tricalcium phosphate (αTCP); beta-tricalcium phosphate (βTCP); mixtures of alpha-tricalcium phosphate (αTCP) and beta-tricalcium phosphate (βTCP), finally more specifically the materials mentioned above and forming the subject matter of patents IT-1 307 292 and EP-1 411 035 (and the corresponding application for an Italian patent B02002A000650).

The following is a description of several examples of applications of the invention, provided by way of example only and without limiting the scope of the invention.

In a first example, the made to measure prosthetic device has the following application: reconstruction of extensive sections of the cranial theca (neurosurgery).

Accidents involving head trauma have become particularly frequent in recent years proportional with the increase in road traffic, accidents at the workplace or during leisure time. Serious head traumas often involve brain function, which takes priority over other lesions, whose future preservation becomes the neurosurgeon's priority.

A second cause may be skin tumours or rejection phenomena following the use of other materials, for which the treatment requires surgical removal as a last resort.

In all of these cases the surgical treatment is based on the removal of extensive sections of bone tissue with consequent primary problems of brain safety and, second in order of priority, aesthetic implications.

To solve and overcome these clinical problems, for reconstruction of the cranial theca a prosthetic device was produced, which forms the subject matter of the present invention, "made to measure" and identical to the lacuna in the bone to be filled, using hydroxyapatite with controlled and interconnected porosity (45-65%) with objective clinical evidence showing immediate advantages, from an aesthetic viewpoint, but above all in terms of biocompatibility, which other materials cannot fully guarantee.

The surgical technique, not innovative in itself, involves detachment of tissues from the edge of the defect and insertion of the made to measure prosthesis by slotting into place; fixing it with simple wiring thanks to the holes in the "made to measure" prosthesis.

In a second example, the made to measure prosthetic device has the following application: lifting the buccal cavity (dental surgery).

Loss of the upper back teeth often leads to vertical bony atrophy of the alveolar ridge to a certain extent, such that titanium implants cannot be inserted. Today, it is already possible to successfully lift the buccal cavity by means of bone graft according to the Caldewell—Luc technique, but insertion of implants in a single step cannot also be guaranteed.

Therefore, in these cases the buccal cavity lift is normally done first, using autologous or homologous bone, then insertion of the implants after 6 months.

However, observing biological principles, it is possible to use "made to measure prostheses" made of hydroxyapatite with controlled and interconnected porosity (40-60%) which allow immediate insertion of the titanium implant, at the same time allowing clotting and its transformation into bone.

The clinical example involved the use of a prosthetic device disclosed, "made to measure" using hydroxyapatite with controlled and interconnected porosity (40-60%) which made it possible to insert the titanium implants in a single step, thus achieving a primary stability that would otherwise be difficult.

The surgical technique, also not innovative in itself, involves opening of the buccal cavity from the side and insertion of the made to measure prosthesis in the space obtained.

In a third example, the made to measure prosthetic device has the following application:
ceramic support (scaffold) on which staminal cells can be "sown" for repairing long bones (orthopaedic surgery, maxillofacial surgery).

Progress in knowledge of cellular biology and improvements in culture techniques make it possible to imagine and in some cases achieve in vitro reconstruction of skeletal tissues able to substitute sick ones.

In the specific case for this application a pre-shaped device was produced using hydroxyapatite with controlled and interconnected porosity (55-85%) modelled, with the same design and production criteria as the previous examples, in the dimensions and shape of the sick bone to be substituted and able to be attached to the staminal cells previously taken from the patient's bone marrow then expanded in vitro.

With this system, hydroxyapatite with controlled and interconnected porosity is used as a "scaffold" in which the staminal cells (expanded in vitro) are placed. Once they make contact with the ceramic support, the staminal cells start proliferating, becoming different and generating new bone tissue. The next step, as in the other cases, consists of surgically replacing the sick or damaged bone with this synthetic—organic bone. Again, the operating technique, not innovative in itself, involves substitution of the damaged section with a made to measure prosthesis (to which the autologous staminal cells were previously added) secured by a Kirsh thread or by wiring.

The positive results of these transplants are guaranteed by the use of a synthetic material (Ca/P compounds such as: stoichiometric hydroxyapatite, non-stoichiometric hydroxyapatite, carbonated hydroxyapatite, doped hydroxyapatites, tricalcium phosphate or mixtures of them) chemically similar to the inorganic component of the bone tissue and of cells which the immune system recognises as its own. With the passage of time (several months) the "device" surgically inserted is slowly transformed into bone, binding perfectly with the surrounding tissue.

This material constitutes, by the interconnections of the channels, the ideal foundation for allowing the growth of bone tissue inside it, since it acts as a vascular support for the newly formed tissue, also promoting bone mineralization for the specific dimensions of the pores.

The part of the bone missing is substituted by an identical segment of bone perfectly similar to the part removed, but made synthetically in a laboratory and no longer removed from other individuals.

Moreover, another advantage of the bone device disclosed is that it may form a support (scaffold) for the connection to it of cells and/or growth factors in order to create an osteoinductive effect and/or a support for "drug release" with which drugs and/or chemotherapeutic substances can be associated in medical or oncological therapies.

In the case of flat bones (like those of the cranium) the preferred material is a ceramic of the type described in Italian patent IT-1 307 292, that is to say, a ceramic material with less porosity and greater mechanical strength.

In the case of long bones (for example the femur) the preferred material is a ceramic of the type described in the application for a European patent EP-1 411 035 (and in the corresponding application for an Italian patent B02002A000650), that is to say, a ceramic material with greater porosity which acts as a scaffold for bone restructuring.

The invention described is subject to modifications and variations without thereby departing from the scope of the inventive concept as described in the claims.

The invention claimed is:

1. A method for the production of a biologically active prosthetic device for the reconstruction of bone tissue, comprising the following steps:
    scanning a patient with CAT (Computerised Axial Tomography) in order to obtain a three-dimensional electronic model of a part of the bone and of a bone defect to be reconstructed;
    on the basis of the three-dimensional electronic model, producing prototype resin model of an area of the patient's bone involved by means of a three-dimensional stereolithographic technique;
    by using the prototype resin model, forming a model of the patient's bone defect to be reconstructed;
    forming a negative mould by using slip casting forming technology on the basis of the model of the patient's bone defect to be reconstructed, said negative mould being a negative of the patient's bone defect to be reconstructed;
    by using the negative mould, producing a sintered ceramic semi-finished product, the dimensions and shape of the semi-finished product being slightly larger than those of the bone defect, the sintered ceramic semi-finished product having a controlled and interconnected porosity of from 30 to 90%, said porosity having a bimodal distribution of the pore dimensions in a first range of from 0.1 to 125 microns and in a second range of from 125 to 2500 microns;
    mechanically processing and manually finishing the sintered semi-finished product to obtain a finished ceramic product having precise dimensions and shape of the bone defect; checking the finished product in terms of dimensions and shape directly on the prototype resin model and by using the negative mold.

2. The method according to claim 1, wherein the step of mechanically processing and manually finishing is carried out by removing excess material using diamond milling cutters which turn at high speed.

3. The method according to claim 1, wherein the negative mould of the patient's bone defect comprises means able to detect any points of contact between the semi-finished product and the mould.

4. The method according to claim 3, wherein the means able to detect any points of contact between the semi-finished product and the mould comprise a coating of tracing paper which is coloured at points of contact.

5. The method according to claim 1, wherein the sintered ceramic semi-finished product is made from a Ca/P compound-based biologically active ceramic material.

6. The method according to claim 5, wherein the Ca/P compound-based biologically active ceramic material is selected from the group consisting of: stoichiometric hydroxyapatite; non-stoichiometric hydroxyapatite: carbonated hydroxyapatite (mainly of type B); hydroxyapatite enriched with magnesium or fluoride or with strontium or sodium; carbonated hydroxyapatite enriched with magnesium; hydroxyapatite/β tricalcium phosphate in proportions of 50%-50%, 70%-30%, 30%-70%; alpha-tricalcium phosphate ($\alpha$TCP); beta-tricalcium phosphate ($\beta$TCP); mixtures of alpha-tricalcium phosphate ($\alpha$TCP) and beta-tricalcium phosphate ($\beta$TCP).

7. The method according to claim 1, further comprising a step of final checking the finished ceramic product, in terms of dimensions and shape, the checking being carried out on the prototype resin model and by using the negative mould.

8. A biologically active prosthetic device for reconstructing a bone tissue obtained according to the method of claim 1, wherein the shape and dimensions derive from a model of the area of the patient's bone involved, said model being obtained using rapid prototyping technology; and wherein said prosthetic device has a structure with predetermined and interconnected porosity of from 30 to 90% with bimodal distribution of the dimensions of the pores in a first range of from 0.1 to 125 microns and in a second range of from 125 to 2500 microns, wherein said prosthetic device is made of Ca/P-based ceramic synthesis material using technologies for the impregnation/imbibition of porous supports (cellulose, polyurethane, resin), gel-casting, low pressure injection moulding.

9. The prosthetic device according to claim 8, wherein said prosthetic device is made of a ceramic material selected from the group consisting of: stoichiometric hydroxyapatite; non-stoichiometric hydroxyapatite; carbonated hydroxyapatite (mainly of type B); hydroxyapatite enriched with magnesium or fluoride or with strontium or sodium; carbonated hydroxyapatite enriched with magnesium; hydroxyapatite/$\alpha$ tricalcium phosphate in proportions of 50%-50%, 70%-30%, 30%-70%; alpha-tricalcium phosphate ($\alpha$TCP); beta-tricalcium phosphate ($\beta$TCP); mixtures of alpha-tricalcium phosphate ($\alpha$TCP) and beta-tricalcium phosphate ($\beta$TCP).

10. The prosthetic device according to claim 8, wherein said prosthetic device constitutes a support (scaffold) for attaching cells and/or growth factors in order to create an osteoinductive effect and/or a support for "drug release" with which drugs and/or chemotherapeutic substances may be associated in medical or oncological therapies.

* * * * *

UNITED STATES PATENT AND TRADEMARK OFFICE
CERTIFICATE OF CORRECTION

PATENT NO. : 8,172,907 B2
APPLICATION NO. : 10/594941
DATED : May 8, 2012
INVENTOR(S) : Roberta Martinetti et al.

It is certified that error appears in the above-identified patent and that said Letters Patent is hereby corrected as shown below:

At column 8, line 42, claim 9, after "magnesium;", please delete "hydroxyapatite/$\alpha$" and insert therefor --hydroxyapatite/$\beta$--.

Signed and Sealed this
Thirteenth Day of November, 2012

David J. Kappos
*Director of the United States Patent and Trademark Office*